United States Patent [19]

Vacanti et al.

[11] Patent Number: 5,041,138

[45] Date of Patent: Aug. 20, 1991

[54] NEOMORPHOGENESIS OF CARTILAGE IN VIVO FROM CELL CULTURE

[75] Inventors: Joseph P. Vacanti, Winchester; Charles A. Vacanti, Lexington; Robert S. Langer, Newton, all of Mass.

[73] Assignees: Massachusetts Institute of Technology, Cambridge; Children's Hospital, Boston, both of Mass.

[21] Appl. No.: 339,155

[22] Filed: Apr. 17, 1989

Related U.S. Application Data

[63] Continuation-in-part of Ser. No. 123,579, Nov. 20, 1987, abandoned, which is a continuation-in-part of Ser. No. 933,018, Nov. 20, 1986, abandoned.

[51] Int. Cl.$^5$ .................... A61F 2/28; A61F 2/18; C07C 245/00; A61K 37/00
[52] U.S. Cl. .................... 623/16; 623/10; 623/18; 424/548; 514/21; 530/840
[58] Field of Search .................... 623/16, 66, 11, 15, 623/10, 18; 424/548; 514/21, 801; 128/DIG. 8; 530/840; 435/240.2

[56] References Cited

U.S. PATENT DOCUMENTS

| | | |
|---|---|---|
| 4,144,126 | 3/1979 | Burbidge . |
| 4,228,243 | 10/1980 | Iizuka . |
| 4,356,261 | 10/1982 | Kuettner . |
| 4,485,097 | 11/1984 | Bell . |
| 4,553,272 | 11/1985 | Mears . |
| 4,563,350 | 1/1986 | Nathan et al. .................... 623/16 X |
| 4,609,551 | 9/1986 | Caplan et al. .................... 623/16 X |
| 4,627,853 | 12/1986 | Campbell et al. .................... 623/16 |
| 4,642,120 | 2/1987 | Nevo et al. .................... 623/16 |
| 4,713,070 | 12/1987 | Mano . |
| 4,757,017 | 7/1988 | Cheung . |
| 4,778,749 | 10/1988 | Vasington et al. . |
| 4,846,835 | 7/1989 | Grande .................... 623/11 |

FOREIGN PATENT DOCUMENTS

| | | |
|---|---|---|
| 86116047.7 | 11/1986 | European Pat. Off. . |
| 62-011459 | 1/1987 | Japan . |
| 63-074498 | 4/1988 | Japan . |
| 63-196273 | 8/1988 | Japan . |
| 63-196595 | 9/1988 | Japan . |
| PCT/US87/-00869 | 4/1987 | PCT Int'l Appl. . |
| PCT/US88/-02447 | 7/1988 | PCT Int'l Appl. . |

OTHER PUBLICATIONS

Ptasinska-Urbanska, et al., *Exp. Eye Res.*, vol. 24, No. 3, pp. 241-247 (1977).
J. M. Wozney, et al., *Science* 242, 1528-1534 (Dec. 16, 1988).
J. Upton, *Plastic and Reconstructive Surgery* 68(2), 166-174 (1981).
Alberts, et al., *Molecular Biology of the Cell*, 893 and 894 (1983).

Primary Examiner—Alan Cannon
Attorney, Agent, or Firm—Kilpatrick & Cody

[57] ABSTRACT

Methods and artificial matrices for the growth and implantation of cartilaginous structures and surfaces are disclosed. In the preferred embodiments, chondrocytes are grown on biodegradable, biocompatible fibrous polymeric matrices. Optionally, the cells are proliferated in vitro until an adequate cell volume and density has developed for the cells to survive and proliferate in vivo. One advantage of the matrices is that they can be cast or molded into a desired shape, on an individual basis, so that the final product closely resembles a patient's own ear or nose. Alternatively, flexible matrices can be used which can be manipulated at the time of implantation, as in a joint, followed by remodeling through cell growth and proliferation in vivo. The cultured cells can also be maintained on the matrix in a nutrient media for production of bioactive molecules such as angiogenesis inhibiting factor.

22 Claims, 6 Drawing Sheets

NEOMORPHOGENESIS OF CARTILAGE IN VIVO FROM CELL CULTURE

The United States Government has rights in this invention by virtue of NIH grant No. 26698.

BACKGROUND OF THE INVENTION

This a continuation-in-part of U.S. Ser. No. 123,579 entitled Chimeric Neomorphogenesis of Organs by Controlled Cellular Implantation Using Artificial Matrices filed Nov. 20, 1987 by Joseph P. Vacanti and Robert S. Langer now abandoned which is a continuation-in-part of U.S Ser. No. 933,018 entitled "Chimeric Neomorphogenesis of Organs Using Artificial Matrices" filed Nov. 20, 1986 by Joseph P. Vacanti and Robert S. Langer, now abandoned.

This invention is generally in the field of medicine and cell culture, and in particular in the area of implantable cartilaginous structures formed on biocompatible artificial matrices U.S. Ser. No. 123,579 entitled Chimeric Neomorphogenesis of Organs by Controlled Cellular Implantation Using Artificial Matrices filed Nov. 20, 1987, and U.S. Ser. No. 933,018 entitled "Chimeric Neomorphogenesis of Organs Using Artificial Matrices" filed Nov. 20, 1986, by Joseph P. Vacanti and Robert S. Langer describe a method and means whereby cells having a desired function are grown on polymer scaffolding using cell culture techniques, followed by transfer of the cellpolymer scaffold into a patient at a site appropriate for attachment, growth and function, after attachment and equilibration, to produce a functional organ equivalent. Success depends on the ability of the implanted cells to attach to the surrounding environment and to stimulate angiogenesis. Nutrients and growth factors are supplied during cell culture allowing for attachment, survival or growth as needed.

After the structure is implanted and growth and vascularization take place, the resulting organoid is a chimera formed of parenchymal elements of the donated tissue and vascular and matrix elements of the host. The polymer scaffolding used for the initial cell culture is constructed of a material which degrades over time and is therefore not present in the chimeric organ. Vascular ingrowth following implantation allows for normal feedback mechanisms controlling the soluble products of the implanted cells. The preferred material for forming the matrix or support structure is a biodegradable artificial polymer, for example, polyglycolic acid, polyorthoester, or polyanhydride, which is degraded by hydrolysis at a controlled rate and reabsorbed. These materials provide the maximum control of degradability, manageability, size and configuration. In some embodiments these materials are overlaid with a second material such as gelatin or agarose to enhance cell attachment. The polymer matrix must be configured to provide both adequate site for attachment and adequate diffusion of nutrients from the cell culture to maintain cell viability and growth until the matrix is implanted and vascularization has occurred The preferred structure for organ construction is a branched fibrous tree-like structure formed of polymer fibers having a high surface area, which results in a relatively shallow concentration gradient of nutrients, wastes, and gases, so as to produce uniform cell growth and proliferation.

U.S. Ser. No. 933,018 and U.S. Ser. No. 123,579 disclose several examples of the successful culturing and implantation of hepatocytes, intestine, and pancreas cells, with subsequent normal function, including production and secretion of bioactive molecules. Examples of such molecules include growth hormone from pituitary cells, insulin and glycogen from pancreatic cells, and clotting factors from liver cells. As described in these applications, however, there is a need for a different type of functioning "organ", one which provides primarily a structural function Examples of types of cells which are useful in these applications include cartilage, bone, and muscle cells.

Damage of cartilage produced by disease, such as arthritis, or trauma is a major cause of physical deformity and debilitation. In medicine today, the primary therapy for loss of cartilage is replacement with a prosthetic material, such as silicone for cosmetic repairs, or metal alloys for joint relinement. Placement of prostheses is commonly associated with significant loss of underlying tissue and bone without recovery of the full function allowed by the original cartilage, as well as the irritating presence of a foreign body. Other long term problems associated with a permanent foreign body can include infection, erosion and instability. The lack of truly biocompatible, functional prosthesis can have profound and tragic effects for those individuals who have lost noses or ears due to burns or trauma, such as car accidents or war. The best surgeons can do for these patients is to carve a piece of cartilage out of a piece of lower rib to approximate the necessary contours and insert it into a pocket of skin in the area where the nose or ear is missing.

In the past, bone has been replaced using actual segments of sterilized bone or bone powder or porous surgical steel seeded with bone cells which were then implanted. An example of a process using bone powder and a hydrated collagen lattice is U.S. Pat. No. 4,485,097 to Bell. An example of the implantation of a seeded porous metal prosthesis is U.S. Pat. No. 4,553,272 to Mears. The success of these implants has been limited, in part because of the non-degradable nature of the cell supports. Very little of anything has ever been actually used to replace the cartilage overlaying bone surfaces. At this time, when cartilage is worn or damaged in a joint, there is no way to replace the cartilage. Although several preparations are being tested to stimulate growth and repair of the remaining cells, in most cases repair to injuries is made surgically. Patients suffering from degeneration of cartilage can only turn to pain killers or antiinflammatories for relief.

To date, the growth of new cartilage from either transplantation of autologous or allogeneic cartilage has been largely unsuccessful. Microscopic islands of cartilage formation have recently been demonstrated histologically in vivo by implanting recombinant bone morphogenic protein, as reported by J. M. Wozney, et al., Science, 242, 1528-1534, (Dec. 16, 1988). Limited success has been achieved in making neocartilage using free autogenous grafts of perichondrial flaps, as described by J. Upton, *Plastic and Reconstructive Surgery*, 68(2), 166-174, (August 1981). However, there have been no reports of successful growth of cartilage in vivo from cell culture.

It is therefore an object of the present invention to provide a method and means for designing, constructing and utilizing artificial matrices as temporary scaffolding for cellular growth and implantation of cartilage.

It is a further object of the invention to provide biodegradable, non-toxic matrices which can be utilized for cell growth, both in vitro and in vivog, as supports for cartilaginous structures.

It is a still further object of the invention to provide biodegradable, non-toxic matrices which can be utilized for cell growth, both in vitro and in vivog, to replace degenerated cartilage in joints and other places of surface-to-surface contact.

It is another object of this invention to provide an in vitro system in which cells will retain their normal morphology and cell function for the secretion of bioactive molecules normally produced in the body by those cells.

SUMMARY OF THE INVENTION

Methods and artificial matrices for the growth and implantation of cartilaginous structures and surfaces and the production of bioactive molecules manufactured by chondrocytes are disclosed.

In the preferred embodiments, chondrocytes are grown in culture on biodegradable, biocompatible fibrous matrices formed of polymers such as polyglycolic acid, polylactic acid, or other polymers which degrade over time as a function of hydrolysis of the polymer backbone into innocuous monomers. The matrices are designed to allow adequate nutrient and gas exchange to the cells until engraftment and vascularization at the site of engraftment occurs. The cells can be cultured in vitro until an adequate cell volume and density has developed for the cells to survive and proliferate in vivo, or maintained in vitro for the purpose of manufacturing bioactive molecules, such as angiogenesis inhibiting factor. Alternatively, when adequate cell numbers for implantation are available, the cells can be attached to the matrix and implanted directly, without proliferation in vitro. One advantage of the matrices is that they can be cast or molded into a desired shape on an individual basis, so that the final product closely resembles the patient's own ear or nose, or flexible matrices can be used which allow for manipulation at the time of implantation, as in a joint, followed by remodeling through cell growth and proliferation in vivo.

BRIEF DESCRIPTION OF THE DRAWINGS

FIG. 2 is a phase contrast photomicrograph of bovine chondrocytes attached to two polymer fibers three hours after seeding the fibers.

FIG. 3 is a photograph of Hematoxylin and Eosin stained chondrocytes after 10 days in culture.

FIGS. 4a and 4b are phase micrographs of chondroxytes attached to the polymer fibers after 21 days in culture. FIG. 4a is a 4× magnification. FIG. 4b is a 20× magnification.

FIG. 5 is a photomicrograph of polyglactin 910 fibers shaped and seeded with bovine chondrocytes and cultured in nude mice, after 8, 18, 28, 49 and 81 days.

FIG. 6 is a photograph at 4× of Hematoxylin and Eosin stained chondrocytes showing a small island of cartilage at the arrow eight days after implantation.

FIG. 7 is a photograph at 20× of the cartilage island of FIG. 6.

FIG. 8 is a photograph at 20× of Hematoxylin and Eosin stained chondrocytes on a polymeric matrix 28 days after implantation, showing the polymers being absorbed by the surrounding tissue.

FIGS. 9a and 9b are photographs of Hematoxylin and Eosin stained chondrocytes 81 days after implantation in an animal. FIG. 9a is at 20×. FIG. 9b is at 4×.

DETAILED DESCRIPTION OF THE INVENTION

Figure 1A:
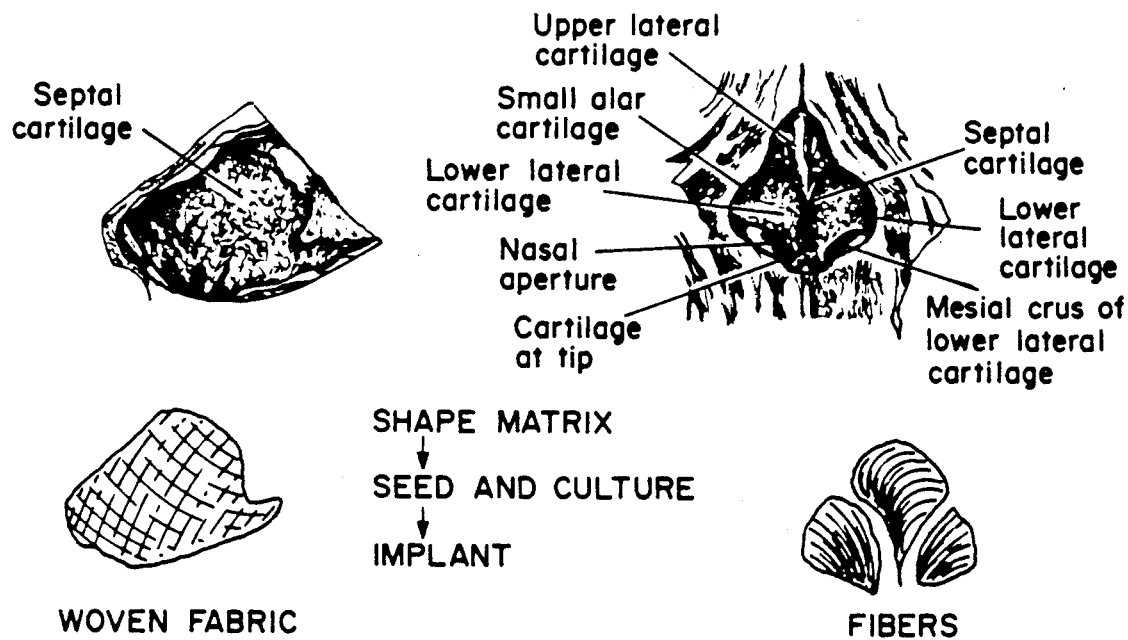
FIG. 1 is a schematic of the construction of a biodegradable matrix seeded with chondrocytes for use as parts of a replacement nose (FIG. 1A) or ear (FIG. 1B), according to the method of the present invention.

U.S. Ser. No. 123,579 entitled Chimeric Neomorphogenesis of Organs by Controlled Cellular Implantation Using Artificial Matrices filed Nov. 20, 1987 by Joseph P. Vacanti and Robert S. Langer, which is a continuation-in-part of U.S. Ser. No. 933,018 entitled "Chimeric Neomorphogenesis of Organs Using Artificial Matrices" filed Nov. 20, 1986 by Joseph P. Vacanti and Robert S. Langer, describes a technique of placing dispersed cell types onto synthetic biodegradable polymer fibers in vitro which have been configured to produce high cell densities by allowing adequate diffusion of nutrients and waste as well as gas exchange. This technique has been applied to chondrocytes for the purpose of creating an implant of cartilage.

Cartilage is a specialized type of dense connective tissue consisting of cells embedded in a matrix. There are several kinds of cartilage. Hyaline cartilage is a bluish-white, glassy translucent cartilage having a homogeneous matrix containing collagenous fibers which is found in articular cartilage, in costal cartilages, in septum of the nose, in larynx and trachea. Articular cartilage is hyaline cartilage covering the articular surfaces of bones. Costal cartilage connects the true ribs and the sternum. Fibrous cartilage contains collagen fibers. Yellow cartilage is a network of elastic fibers holding cartilage cells which is primarily found in the epiglottis, the external ear, and the auditory tube. As described below, cartilage implants can be formed of one or more types of cartilage, depending primarily on the location of the implant and the type of cartilage cells seeded onto the polymeric matrix.

In the preferred method, polymer fibers are placed in culture media containing chondrocytes, where the chondrocytes attach to the fibers in multiple layers and retain their normal rounded configuration, which appears to be essential for the chondrocytes to maintain their normal function and secrete a cartilage matrix and other bioactive molecules such as angiogenesis inhibiting factor. This technique also allows transplantation of the polymer cell scaffold into animals without disrupting the complex of attached chondrocytes. Transplantation of this complex containing a high density of normally functioning chondrocytes with a large surface area into an animal allows the cells to obtain adequate nutrition by diffusion and successful engraftment of functioning chondrocytes with cartilage formation even in the initial absence of vascularization.

The examples below demonstrate that it is possible to grow in culture on fibers of biodegradable polymers chondrocytes that appear to be morphologically and functionally normal, and will proliferate to a cell density sufficient to allow implantation of the cell polymer scaffold in animals and successful engraftment with formation of a new tissue equivalent as the polymer resorbs. Visual and histologic characterization of this tissue show that it is hyaline cartilage, very similar to normal human fetal cartilage. The examples also demonstrate that the polymer fiber scaffold is essential in that neither injection of free chondrocytes nor implantation of the polymer fibers without attached chondrocytes results in cartilage formation. Associated with the development of this cartilage formation is a decrease in neovascularization and fibrous tissue formation, probably reflecting the production of an angiogenesis inhibiting factor by the newly formed cartilage, as has been demonstrated by assays of serum in which chondrocytes have been grown in vitro on fibers.

The method and matrices providing structural and functional cartilage equivalents using bioabsorbable artificial substrates as temporary scaffolding for cellular transfer and implantation reaffirms the principles first outlined in U.S. Ser. No. 123,579 filed Nov. 20, 1987 and U.S. Ser. No. 933,018:

1. Every structure in living organisms is in a dynamic state of equilibrium, undergoing constant renewal, remodeling and replacement of functional tissue which varies from organ to organ and structure to structure.

2. Dissociated structural cells tend to reform structure, depending on the environment in which they are placed and the degree of alteration which they have undergone.

3. Cell shape is determined by cytoskeletal components and attachment to matrix plays an important role in cell division and differentiated function. If dissociated cells are placed into mature tissue as a suspension without cell attachment, they may have difficulty finding attachment sites, achieving polarity, and functioning because they begin without intrinsic organization. This limits the total number of implanted cells which can remain viable to organize, proliferate, and function.

The latter principle is a key point in the configuration of the chondrocyte support matrices. For an organ to be constructed in tissue culture and subsequently successfully implanted, the matrices must have sufficient surface area and exposure to nutrients such that cellular growth and differentiation can occur prior to the ingrowth of blood vessels following implantation. After implantation, the configuration must allow for diffusion of nutrients and waste products and for continued blood vessel ingrowth as cell proliferation occurs.

Chondrocytes are initially isolated and cultured using techniques known to those skilled in the art of tissue culture. In contrast to some types of cells, chondrocytes can be seeded directly onto an appropriate matrix and implanted without first proliferating the cells in vitro. If insufficient cell numbers are available for implantation, cells are first cultured in vitro on the matrix. Once the cells have begun to grow and cover the matrix, they are implanted in a patient at a site appropriate for attachment, growth and function. One of the advantages of a biodegradable polymeric matrix is that angiogenic and other bioactive compounds can be incorporated directly into the matrix so that they are slowly released as the matrix degrades in vivo. As the cell-polymer structure is vascularized and the structure degrades, the cells will differentiate according to their inherent characteristics.

In the preferred embodiment, the matrix is formed of a bioabsorbable, or biodegradable, synthetic polymer such as a polyanhydride, polyorthoester, or polyglycolic acid. In some embodiments, attachment of the cells to the polymer is enhanced by coating the polymers with compounds such as basement membrane components, agar, agarose, gelatin, gum arabic, collagens, fibronectin, laminin, glycosaminoglycans, mixtures thereof, and other materials having properties similar to biological matrix molecules known to those skilled in the art of cell culture. All polymers must meet the mechanical and biochemical parameters necessary to provide adequate support for the cells with subsequent growth and proliferation. Factors, including nutrients, growth factors, inducers of differentiation or dedifferentiation, products of secretion, immunomodulators, inhibitors of inflammation, regression factors, biologically active compounds which enhance or allow ingrowth of the lymphatic network or nerve fibers, and drugs, can be incorporated into the matrix or provided in conjunction with the matrix. Similarly, polymers containing peptides such as the attachment peptide RGD (Arg-Gly-Asp) can be synthesized for use in forming matrices.

A presently preferred polymer is Polyglactin, developed as absorbable synthetic suture material, a 90:10 copolymer of glycolide and lactide, manufactured as Vicryl ® braided absorbable suture (Ethicon Co., Somerville, N.J.) (Craig P. H., Williams J. A., Davis K. W., et al.: A Biological Comparison of Polyglactin 910 and Polyglycolic Acid Synthetic Absorbable Sutures. Surg. 141; 1010, (1975)). Polyglycolide fibers can be used as supplied by the manufacturer. Other shapes can be fabricated using one of the following methods:

Solvent Casting. A solution of polymer in an appropriate solvent, such as methylene chloride, is cast as a branching pattern relief structure. After solvent evaporation, a thin film is obtained.

Compression Molding. Polymer is pressed (30,000 psi) into an appropriate pattern.

Filament Drawing. Filaments are drawn from the molten polymer.

Meshing. A mesh is formed by compressing fibers into a felt-like material.

The polymers can be characterized with respect to mechanical properties such as tensile strength using an Instron tester, for polymer molecular weight by gel permeation chromatography (GPC), glass transition temperature by differential scanning calorimetry (DSC) and bond structure by infrared (IR) spectroscopy; with respect to toxicology by initial screening tests involving Ames assays and in vitro teratogenicity assays, and implantation studies in animals for immunogenicity, inflammation, release and degradation studies. In vitro cell attachment and viability can be assessed using scanning electron microscopy, histology, and quantitative assessment with radioisotopes.

At the present time, a mesh-like structure formed of fibers which may be round, scalloped, flattened, star shaped, solitary or entwined with other fibers is preferred. The use of branching fibers is based upon the same principles which nature has used to solve the problem of increasing surface area proportionate to volume increases. All multicellular organisms utilize this repeating branching structure. Branching systems represent communication networks between organs as well as the functional units of individual organs. Seeding and implanting this configuration with cells allows implantation of large numbers of cells, each of which is exposed to the environment of the host, providing for free exchange of nutrients and waste while neovascularization is achieved.

Figure 1B:
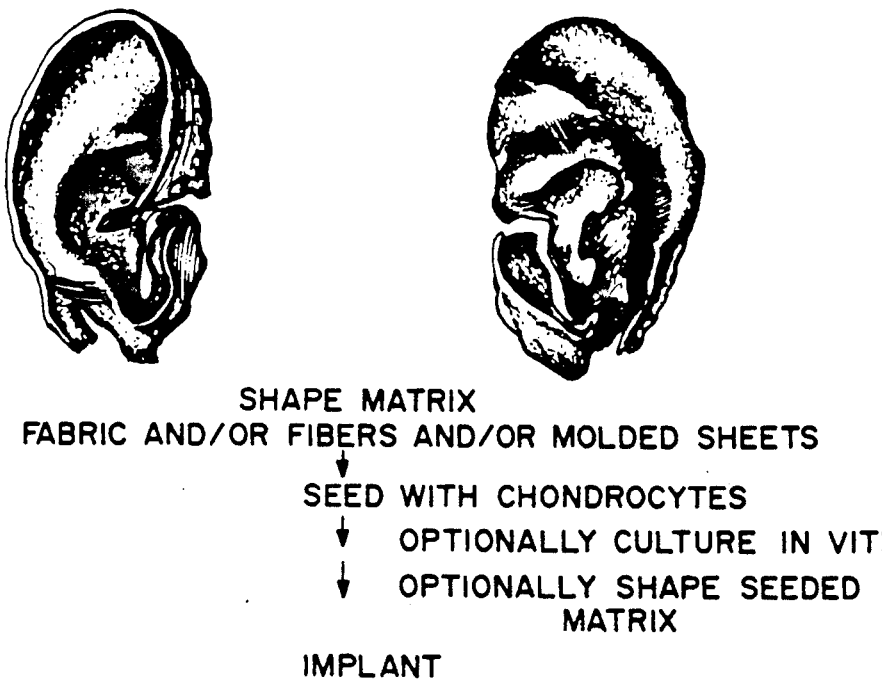

The polymeric matrix may be made flexible or rigid, depending on the desired final form, structure and function. For purposes of making a nose or ear, fibers of sheets of felt-like or solid material are cut to approximate the plates of cartilage, as shown in FIG. 1A or FIG. 1B. For resurfacing a joint, a more flexible fibrous mat is cut to approximate the entire joint surface, then fitted to the joint as necessary during implantation. An apparent advantage of using the fibrous matrices is the ease in reshaping and rearranging the structures at the time of implantation.

An advantage of the present invention is that, using similar technology, other components of the nose, ear and joints can be constructed using bone and nerve cells. For example, matrices in the shape of the bones of the inner ear can be formed by casting the polymer to form hollow shapes of the appropriate size and configuration, then seeding with bone cells, culturing in vitro as required, then implanting into an ear canal. The major portion of the eustachian tube and inner ear is made of cartilage. The technology is equally applicable to manufacture of an ear drum or skin for covering the implanted cartilage. Nerve cells can also be implanted within or in juxtaposition with the reconstructed ear.

Cells may be derived from the host, a related donor or from established cell lines. In one variation of the method using a single matrix for attachment of one or more cell lines, the scaffolding is constructed such that initial cell attachment and growth occur separately within the matrix for each population, for example, bone and chondrocyte cell populations. Alternatively, a unitary scaffolding may be formed of different materials to optimize attachment of various types of cells at specific locations. Attachment is a function of both the type of cell and matrix composition.

As described in U.S. Ser. No. 933,018 and U.S. Ser. No. 123,579, these cell-matrix structures are useful not only for in vivo implantation, but also for the production of bioactive molecules in vitro, such as angiogenesis inhibiting factor.

The following non-limiting examples demonstrate actual attachment of cell preparations to bioerodible artificial polymers in cell culture and implantation and engraftment of this polymer-cell scaffold into animals. The examples further demonstrate that the cells attached to the matrix function normally and secrete bioactive molecules, such as angiogenesis inhibiting factor, and can therefore be used for the in vitro production of such molecules.

Articulating cartilage was obtained from the shoulders of calves under two weeks of age slaughtered earlier in the day. The shoulders were washed in Povidone-Iodine 10% (Betadine, Purdue Frederick Co., Norwalk, Conn.) solution, then, under sterile conditions, the muscle attachments was sharply dissected from the underlying bone to expose the joint surfaces. The cartilage from the articulating surfaces of the joint were sharply dissected from the underlying bone using a #10 scalpel (Bard-Parker, Rutherford, New Jersey). The cartilage was cut into pieces with dimensions of less than 5 mm per side and washed twice in Phosphate Buffered Saline (PBS) with electrolytes and adjusted to neutral pH. The cartilage was then incubated at 37° C. in a solution of 0.2% clostridial collagenase (Worthington CLS II, 140 U/mg) and agitated overnight as described by Klagsbrun, (*Methods in Enzymologgy*, Vol. VIII). This suspension was then filtered using a 153 $\mu$g nylon sieve (Tetko, Elmford, N.Y. 10523). The cells were then removed from suspension using centrifugation, washed twice with PBS solution and counted with a hemocytometer. The solution was centrifuged at 1800 rpm and the supernatant above the cell suspension was removed via suction using a micro pipette until the volume of the solution yielded a chondrocyte concentration of $5 \times 10^7$ cells/cc.

Braided threads of polyglactin 910, a 90-10 copolymer of glycolide and lactide, coated with polyglactin 370 and calcium stearate ("0" vicryl suture material, Ethicon Co., Somerville, N.J.) were then cut into pieces of approximately 17 mm in length. One end was unbraided to expose multiple fibers, 14 microns in diameter. A knot was placed at the other end to aid in locating the polymer during subsequent biopsy. Two polymer fibers were placed into each of 26 Falcon tissue culture dishes, 35 mm in size. Two hundred $\mu$L of the above solution was placed on the two fibers in each of 15 wells, thus exposing 30 fibers to the solution containing chondrocytes (the experimentals) and keeping 22 polymers free from exposure to chondrocytes (the controls). Next, 2 cc of a solution containing Hamm's F-12 culture media and 10% fetal calf serum with L-glutamine (292 $\mu$g/cc), penicillin (100 U/cc), streptomycin (100 $\mu$g/cc) and ascorbic acid (5 $\mu$g/cc) was added to each well. After being incubated at 37° C. for 3, 6, 11, 18, 21 and 28 days, six fibers from each group were examined grossly for the presence and morphologic appearance of chondrocytes using phase contrast microscopy and then evaluated histologically using Hematoxylin and Eosin staining and Aldehyde-Alcian Fuschin stain for chondroitin sulfate, the strongly acidic sulfate of mucopolysaccharides of the cartilage.

FIG. 2 is a phase contrast photomicrograph of bovine chondrocytes attached to two polymer fibers three hours after seeding the fibers. It is important to note that the chondrocytes appear round, their normal configuration. This configuration is necessary for secretion of the components of cartilage. FIG. 3 is a photograph of the cells stained with Hematoxylin and Eosin after 10 days in culture. FIG. 4a and 4b are phase micrographs of the cells attached to the polymer fibers after 21 days in culture. It appears that the chondrocytes cause the fibers to bend on themselves and come into contact with other chondrocytes. FIG. 4a is a 4× magnification showing the very high density of chondrocytes filling in the spaces between the polymer fibers. FIG. 4b is a 20× magnification showing that when the chondrocytes come to the end of a polymer fiber they seem to multiply to a certain density and form what looks like a node. After 24 days in culture, the matrix between these cells stained basophilic by hematoxylin Eosin staining, demonstrating the presence of cartilage. The cells are further spaced apart after 24 days in culture than after 10 days. Phase microscopy of cells after four weeks in culture shows the chondrocytes bridging the distances between the polymer fibers.

The remaining forty fibers (24 experimental and 16 control) were surgically implanted subcutaneously on the dorsum of 40 male nude mice (Athymic NCr/nude/Sde, Dept. of Radiation Medicine Massachusetts General Hospital, Boston, MA), 4–5 weeks of age, in the midline at the base of the neck. Thirty-five of these implants (19 experimentals and 16 controls) were done after the fibers had been incubated for three days in vitro, while the remaining five, all experimentals, were done after incubating the fibers for 10 days in vitro. Five mice with implants (one control, one with chondrocytes incubated for 10 days and three with chondrocytes incubated for three days) were sacrificed at each of the following intervals: 8, 18, 28, 49 and 81 days. The implants were then excised from the surrounding tissue with sharp dissection utilizing a tissue plane which easily separated the implant from the surrounding tissue. The specimens thus included primarily implanted tissue and minimal endogenous tissue from the animal.

Each specimen was fixed in formalin, weighed, and its volume calculated by measuring the volume of a liquid which it displaced. Their weights and volumes were correlated and plotted against time. All specimens were evaluated grossly and histologically, using Hematoxylin and Eosin stains as well as an Aldehyde-Alcian Fuschin stain for the presence of chondroitin sulfate, a major component of cartilage.

FIG. 5 is a photomicrograph of polyglactin 910 fibers seeded with bovine chondrocytes and cultured in nude mice, after 8, 18, 28, 49 and 81 days. FIG. 6 is a 4× photograph of Hematoxylin and Eosin stained cells after 8 days implantation showing a small island of cartilage at the arrow. FIG. 7 is a photograph at 20× of the cartilage island of FIG. 6. FIG. 8 is a photograph at 20× of an implant after 28 days, showing the polymers being absorbed by the surrounding tissue. FIG. 9a is a photograph at 20× after implantation in an animal for 81 days. FIG. 9b is the same implant at 4×, looking very similar to normal human fetal cartilage at 10 weeks.

In a control study, ten mice were injected subcutaneously in the same region with a 200 µL suspension containing $5 \times 10^5$ chondrocytes, without attachment to polymers. Five of these suspensions contained chondrocytes isolated primarily from the calf shoulder and then injected into the mice. The other five suspensions contained chondrocytes obtained at the same isolation and then incubated in vitro for three days prior to injection. These mice were sacrificed at similar time intervals, and the areas injected were evaluated histologically in the same manner for evidence of chondrocytes or cartilage.

The results demonstrate that chondrocytes attach to synthetic biodegradable polymer fibers in cell culture and proliferate to a cell density sufficient to allow implantation of the cell polymer scaffold in animals with successful engraftmen and cartilage formation. Fibers of polyglactin 910 incubated in culture media in the presence of bovine chondrocytes had chondrocytes adhering to them and were surgically implanted subcutaneously on the dorsum of twenty nude mice. As controls, sixteen sets of fibers, incubated in media not containing chondrocytes, were implanted in the same manner into sixteen nude mice and ten mice were injected with 0.2 cc of culture media containing $5 \times 10^5$ chondrocytes in the same area.

The three groups of mice were sacrificed at 8, 18, 28, 49 and 81 days and the implants were evaluated grossly and histologically. In eighteen of the twenty implants with chondrocytes adhering in vitro, there was histologic evidence of cartilage which progressed over the time course of this study and was indistinguishable in appearance to normal human fetal cartilage. Furthermore, over the time course of this study, the polymer fibers dissolved, beginning by day 27, and, utilizing Hematoxylin and Eosin staining, as well as Aldehyde-Alcian Fuschin stains, the cartilage progressed histologically from being isolated islands of cartilage in the presence of fibrous tissue and neovascularization at day 8, to becoming a homogenous mass of cartilage. Neovascularization of the implant with mild inflammation was seen initially, but over time, the new blood vessels regressed as cartilage matrix was laid down and intercellular chondrocyte distances increased as they do with normal cartilage maturation. The decrease in inflammatory response, as evidenced by decreases in the number of polymorphonuclear leukocytes and giant cells, correlated with the disappearance of the polymers There was very little evidence of either inflammatory response or polymer remnants by day 81.

There was no evidence of cartilage present in any of the control polymeric implants, as determined histologically using Hematoxylin and Eosin stain. A mild inflammatory response with polymorphonuclear leukocytes, giant cells, and fibroblasts was noted until day 28, after which there was no evidence of the implant. Cartilage formation was also not evident in any area injected with chondrocytes in suspension.

In conclusion, the chondrocytes readily adhere to the polymer fibers. The six experimental fibers incubated in vitro with chondrocytes were seen microscopically to have multiple layers of chondrocytes adhering to them sufficiently well that gentle agitation of the complex did not lead to dissociation of the cells from the fibers. The cells appeared to remain in their normal rounded configuration and analysis of the media in which they were grown demonstrated that angiogenesis inhibiting factor was produced by these cells. The number of chondrocytes as well as the number of layers of chondrocytes adhering to the polymer fibers appeared to increase progressively with time and appeared to actively remodel the fiber configuration and bridge small distances between the fibers The six control fibers incubated in vitro without chondrocytes showed no evidence of chondrocytes polyanhydride, polyorthoester, polylactic acid, polyglycolic acid, and combinations thereof. cartilage, until only cartilage with very little evidence of polymer remained and the specimens became a homogeneous mass of cartilage histologically very similar to normal human fetal cartilage. There was a very positive correlation between the weights and volumes in both groups, with a rapid decline in the weights and volumes of the control implants with time after an initial increase in size. The weights and volumes of the experimentals (those polymers with attached chondrocytes) initially paralleled the increase seen in the controls, but then seemed to level off at a stable size by day 49. In the second group of controls, the injections of free chondrocytes in suspension, there was no evidence of cartilage formation in any of the areas injected.

Although this invention has been described with reference to specific embodiments, variations and modifications of the method and means for constructing cartilage implants by culturing chondrocytes on matrices having maximized surface area and exposure to the surrounding nutrient-containing environment will be apparent to those skilled in the art. Such modifications and variations are intended to come within the scope of the appended claims.

We claim:

1. A method for making a cartilaginous structure comprising
    providing a biocompatible, biodegradable synthetic polymeric matrix in a nutrient environment and
    attaching cartilage cells to the matrix to form a cartilaginous structure suitable for implantation into a patient to replace defective or missing cartilage.

2. The method of claim 10 wherein the polymer is selected from the group consisting of on histologic evaluation. In vitro, all polymer fibers (controls and experimentals) began to dissolve by day 27. On gross and histologic examination using Hematoxylin and Eosin stain, none of the 16 specimens designated as controls displayed any evidence of cartilage. In contrast, 18 of 20 specimens in the experimental group showed evidence of cartilage formation grossly, as well as histologically using Hematoxylin and Eosin stain. Histologic examination of the implants removed at day 8 showed the fibers were imbedded in fibrous tissue with evidence of a mild inflammatory response consisting of infiltrates of polymorphonuclear leukocytes and giant cells, and isolated "nests" of cartilage. During the time intervals to day 18 and day 28, these islands of cartilage grew and coalesced into a large homogenous mass of cartilage. There was no evidence of neovascularization in the 49- and 81- day implants, and there was decreasing evidence of an inflammatory response with time as characterized by a decrease in the number of polymorphonuclear leukocytes and giant cells. Very little evidence of the polymer fibers was seen after 28 days. This increase in the size of the cartilage appeared to be at the expense of the fibrous tissue previously seen and associated at least temporarily with a decrease in neovascularization and resolution of the mild inflammatory response originally noted. Also associated with this was the absorption of the biodegradable polymer fibers. In time, the polymer fibers were progressively replaced by 3. The method of claim 1 further comprising coating the polymer with a material selected from the group consisting of basement membrane components, agar, agarose, gelatin, gum arabic, collagens, fibronectin, laminin, glycosaminoglycans, attachment septides, functional equivalents and mixtures thereof.

4. The method of claim 1 further comprising providing cells selected from the group consisting of bone, skin and nerve cells.

5. The method of claim 1 wherein the matrix is formed as a rigid structure.

6. The method of claim 1 wherein the matrix is formed as a flexible structure conformable to a joint surface.

7. The method of claim 1 wherein the nutrient environment is in vivo further comprising attaching the cells on a matrix and implanting the attached cells on the matrix in an animal without first proliferating the cells on the matrix in vitro.

8. The method of claim 1 further comprising attaching the cells on a matrix, proliferating the cells on the matrix in vitro in a nutrient media, then implanting the cells on the matrix in vitro.

9. The method of claim 1 further comprising implanting the structure as part of an ear.

10. The method of claim 1 further comprising implanting the structure as part of a nose.

11. The method of claim 1 further comprising implanting the structure on the surface of a joint.

12. The method of claim 1 for producing bioactive molecules in vitro further comprising culturing the cells on the matrix in vitro in a nutrient medium until bioactive molecule is produced.

13. The method of claim 12 further comprising extracting the bioactive molecule from the nutrient medium.

14. The method of claim 12 further comprising extracting the bioactive molecule from the cells on the matrix.

15. The method of claim 1 further comprising providing a substance in the nutrient environment or polymer and determining if the substance has an effect on the chondrocyte cells.

16. The method of claim 1 further comprising characterizing the effect of the substance on the chondrocyte cells.

17. The method of claim 1 further comprising providing cells capable of differentiating into cartilage cells and inducing differentiation into cartilage cells.

18. The method of claim 4 wherein the cartilage cells are induced to form bone cells.

19. The method of claim 1 wherein the structure is implanted to repair cartilage damaged by inflammation.

20. The method of claim 1 wherein the structure is implanted to repair cartilage damaged by trauma.

21. The method of claim 1 wherein the structure is implanted to repair cartilage damaged by aging.

22. The method of claim 1 wherein the structure is implanted to repair cartilage when is congenitally defective.

* * * * *